US012616427B2

(12) United States Patent
Maule et al.

(10) Patent No.: US 12,616,427 B2
(45) Date of Patent: May 5, 2026

(54) REDUCING AUDIBLE NOISE PRODUCED BY A COMPONENT OF A COMPUTED TOMOGRAPHY IMAGING SYSTEM

(71) Applicant: GE Precision Healthcare LLC, Waukesha, WI (US)

(72) Inventors: Samuel Edward Maule, Waukesha, WI (US); Jonathan Boutot, Waukesha, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 203 days.

(21) Appl. No.: 18/644,773

(22) Filed: Apr. 24, 2024

(65) Prior Publication Data

US 2025/0336110 A1 Oct. 30, 2025

(51) Int. Cl.
*A61B 6/03* (2006.01)
*A61B 6/00* (2024.01)

(52) U.S. Cl.
CPC .................. *A61B 6/03* (2013.01); *A61B 6/44* (2013.01); *G06T 2207/10081* (2013.01)

(58) Field of Classification Search
CPC .................................... A61B 6/03; A61B 6/44
See application file for complete search history.

(56) References Cited

U.S. PATENT DOCUMENTS

| | | | |
|---|---|---|---|
| 6,861,166 B2 | 3/2005 | Sohmer | |
| 10,184,490 B2 | 1/2019 | Fang et al. | |
| 2017/0306984 A1 | 10/2017 | Peterson et al. | |
| 2024/0252135 A1 * | 8/2024 | Rupcich ................ | A61B 6/467 |

FOREIGN PATENT DOCUMENTS

| | | | | | |
|---|---|---|---|---|---|
| CN | 117028276 A | * | 11/2023 | ............. | F04D 17/16 |
| CN | 120827389 A | * | 10/2025 | ........... | G06T 11/005 |
| EP | 4230873 A1 | * | 8/2023 | ........... | F04D 29/665 |
| JP | 2701603 B2 | | 1/1998 | | |
| JP | 6704041 B2 | | 6/2020 | | |

* cited by examiner

*Primary Examiner* — Casey Bryant
(74) *Attorney, Agent, or Firm* — Daugherty & Del Zoppo, Co. LPA

(57) ABSTRACT

A computed tomography imaging system includes a gantry. The computed tomography imaging system further includes a rotating frame rotatably supported in the gantry. The rotating frame includes an X-ray source configured to emit X-ray radiation that traverses an examination region and an X-ray radiation sensitive detector disposed opposite the X-ray source across the examination region and configured to detect X-ray radiation traversing the examination region and generate a signal indicative of the detected X-ray radiation. The computed tomography imaging system further includes at least one component of the gantry or the rotating frame that produces audible noise. The computed tomography imaging system further includes an audible noise reducer configured to reduce the audible noise. The audible noise reducer includes a resonator tuned to a first frequency of the audible noise.

20 Claims, 10 Drawing Sheets

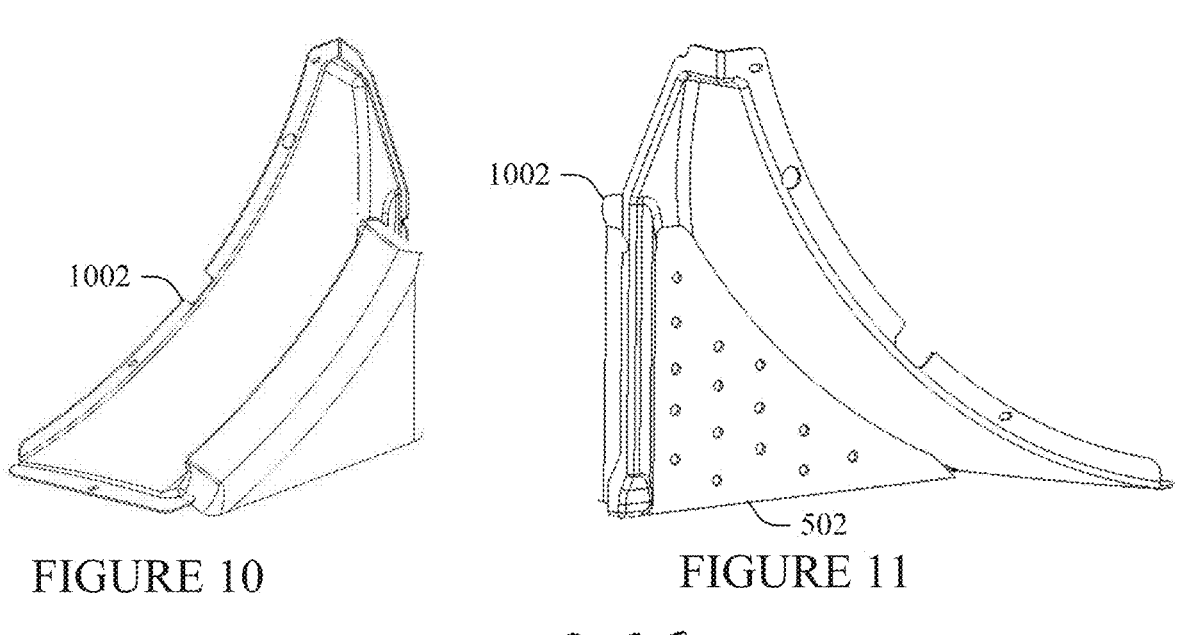
FIGURE 10
FIGURE 11
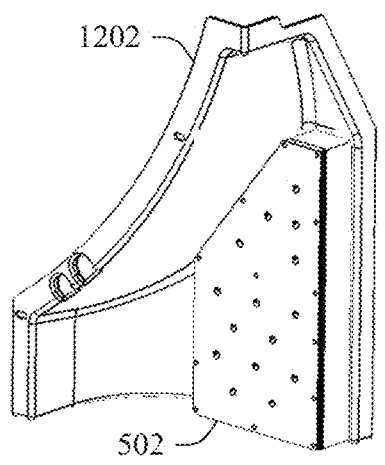
FIGURE 12
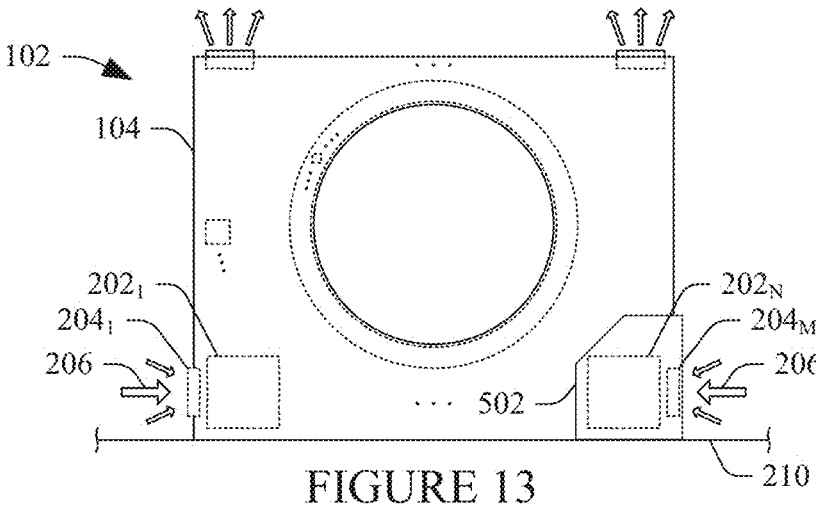
FIGURE 13

REDUCING AUDIBLE NOISE PRODUCED BY A COMPONENT OF A COMPUTED TOMOGRAPHY IMAGING SYSTEM

FIELD

The following generally relates to reducing audible noise produced by an electrical and/or mechanical component of an imaging system, finds particular application to computed tomography (CT), and is also amenable to other imaging modalities and/or other systems.

BACKGROUND

A computed tomography (CT) imaging system includes a stationary frame/gantry that houses electrical and mechanical components utilized in the production, emission and detection of X-rays. For example, the gantry houses a rotating frame that is rotatably supported via a bearing or the like in the gantry, components such as an X-ray source, a high voltage generator, a data acquisition system, a first part of the bearing, etc. are carried on the rotating frame, and other components such as controls, a complementary part of the bearing, etc. are affixed in the gantry. Some of these components produce heat that could be detrimental to components and/or quality of the imaging, if not dissipated. An approach for reducing such heat includes employing an air cooling system with the gantry. For example, a blower and/or a fan has been employed to move air inside of the gantry to carry heat away from components.

Some of these components, during operation (e.g., moving air with blowers and/or fans, rotating the rotating frame, etc.) produce audible noise (i.e., unintended and/or undesired sound in the audible range, twenty (20) to twenty kilohertz (20 kHz), of the electromagnetic spectrum), which may be perceivable by a subject being imaged and/or a clinician operating the imaging system. Air intake blowers, for instance, have produced lower frequency audible noise, such as frequencies lower than six hundred (600) Hz, which can be audibly perceived by the subject and/or the clinician. An approach for reducing audible noise includes utilizing a sound absorber with the imaging system. Unfortunately, such an approach is not well-suited for lower frequencies, which are more difficult to absorb relative to higher frequencies due to their longer wave lengths.

In view of at least the foregoing, there is an unresolved need for an improved approach for reducing audible noise from a component of an imaging and/or other system.

SUMMARY

Aspects described herein address the above-referenced problems and others. This summary introduces concepts that are described in more detail in the detailed description. It should not be used to identify essential features of the claimed subject matter, nor to limit the scope of the claimed subject matter.

In one aspect, a computed tomography imaging system includes a gantry. The computed tomography imaging system further includes a rotating frame rotatably supported in the gantry. The rotating frame includes an X-ray source configured to emit X-ray radiation that traverses an examination region and an X-ray radiation sensitive detector disposed opposite the X-ray source across the examination region and configured to detect X-ray radiation traversing the examination region and generate a signal indicative of the detected X-ray radiation. The computed tomography imaging system further includes at least one component of the gantry or the rotating frame that produces audible noise. The computed tomography imaging system further includes an audible noise reducer configured to reduce the audible noise. The audible noise reducer includes a resonator tuned to a first frequency of the audible noise.

In another aspect, a method includes receiving audible noise at a resonator of an imaging system. The audible noise is produced by a component of the imaging system. The resonator is tuned to a first frequency of the audible noise. The resonator includes a first chamber and a cover with a first region for the first chamber that includes a first set of apertures, a first volume of the first chamber and a first cross-sectional area and a first depth of the apertures of the first set correspond to the first frequency. The method further includes generating, by the resonator, an audible signal at the first frequency and out of phase of the first frequency. The generated signal destructively interferes with the first frequency, thereby reducing the audible noise.

In another aspect, a computer readable medium is encoded with computer executable instructions. The computer executable instructions, when executed by a processor, cause the processor to set a first speed of an intake blower or fan of an imaging system, wherein the intake blower or the fan produces audible noise and set a size of an adjustable size aperture of resonator of an imaging system to resonate at a first frequency of the audible noise corresponding to the first speed.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

FIG. 10 schematically illustrates a non-limiting example of a view of a portion of blower cover from the outside of the imaging system, in accordance with an embodiment(s) herein.

FIG. 11 schematically illustrates a non-limiting example of a view of the portion of the blower cover, with the resonator installed therein, from inside the imaging system, in accordance with an embodiment(s) herein.

FIG. 12 schematically illustrates another non-limiting example of a view of the portion of the blower cover, with the resonator installed therein, from inside the imaging system, in accordance with an embodiment(s) herein.

FIG. 13 schematically illustrates a non-limiting example of the resonator installed with the imaging system, in accordance with an embodiment(s) herein.

DETAILED DESCRIPTION

Embodiments of the present disclosure will now be described, by way of example, with reference to the figures, in which a system, a method and/or a computer readable medium includes instructions for reducing audible noise produced by one or more components of an imaging system includes employing a Helmholtz based resonator turned to at least one frequency of interest corresponding to the audible noise. As discussed above, by way of example, a CT imaging system includes components that produce audible noise, including lower frequency audible noise, that may be audibly perceived by a subject being imaged and/or a clinician operating the imaging system during an imaging examination, and existing approaches such as employing a sound absorber are not well-suited for absorbing the longer wave lengths of lower frequencies of the audible sound range.

The approach described herein reduces audible noise. In one instance, the approach includes a resonator with one or more cavities, each with one or more apertures, where a combination of a cavity volume and an aperture cross-sectional area corresponds to a frequency of interest of the audible noise, and the resonator resonates at the frequency of interest in response to receiving audible noise, which results in the resonator resonating at the frequency of interest, produces pressure waves that destructively interfere with and canceling the frequency of interest in the audible noise. In one instance, the aperture cross-sectional area is a static predetermined value, and, in another instance, the aperture cross-sectional area is dynamic in that a size of the cross-sectional area can match a frequency of the audible noise.

In one instance, the resonator reduces audible noise produced by the CT imaging system, including lower frequency audible noise produced by blowers, fans, etc., as well as other audible noise corresponding to other frequencies in audible sound range, such as frequencies corresponding to rotating the rotating frame and/or components on the rotating frame and/or inside of the gantry. This allows for reducing a level of the audible noise that can be audibly perceived by a subject being imaged and/or a clinician operating the CT imaging system for an imaging examination of the subject, which also allows for increasing blower and/or fan speed, providing further cooling for the system, which can improve system performance.

Figure 1:
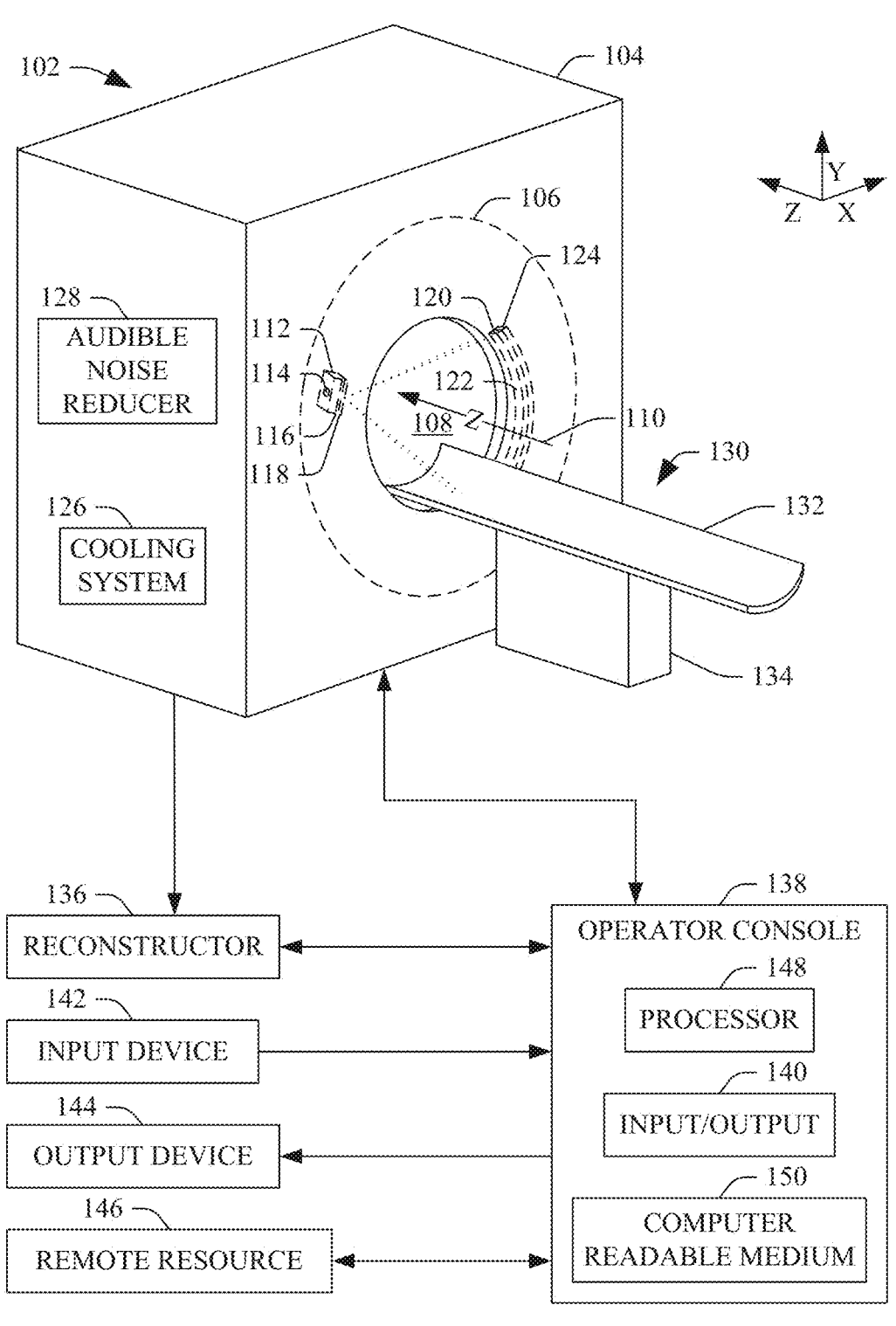
FIG. 1 schematically illustrates a non-limiting example of an imaging system including an audible noise reducer, in accordance with an embodiment(s) herein.

Initially referring to FIG. 1, a non-limiting example of an imaging system 102 such as a computed tomography (CT) imaging system is schematically illustrated. The imaging system 102 includes a generally stationary (i.e., non-rotating) gantry 104 and a rotating frame 106. The rotating frame 106 is rotatably supported in the gantry 104, e.g., via a bearing or the like, and is configured to rotate around an examination region 108 about a rotational or z-axis 110. In some instances, the gantry 104 can be configured to tilt through the z-axis 110. A gantry controller is configured to control rotation (and tilt, if available) of the rotating frame 106, including no rotation.

An X-ray source assembly 112 is supported by the rotating frame 106 and rotates in coordination with the rotating frame 106. The X-ray source assembly 112 includes an X-ray source 114 such as an X-ray tube. The X-ray source 114 is configured to emit X-ray radiation having an energy in the X-ray diagnostic range (e.g., 20 keV to 150 keV). The X-ray assembly 112 may further include or is coupled to a filter 116 that characterizes a radiation dose profile and/or a collimator 118 that shapes the X-ray radiation to form a generally fan, wedge, cone, etc. shaped beam that traverses the examination region 108. An X-ray controller is configured to control components of the X-ray assembly 112 such as radiation emission of the X-ray source 114, the collimator 118, etc.

A radiation sensitive detector array 120 includes a one- or two-dimensional (1-D or 2-D) array of rows of radiation sensitive detector elements 122 and is supported by the rotating frame 106 along an arc opposite the X-ray source 114, across the examination region 108. Each radiation sensitive detector element is in electrical communication with a data acquisition 124. The detector elements include an indirect conversion detector such as a scintillator/photo-diode detector and/or a direct conversion detector such as a Cadmium Telluride (CdTe), a Cadmium Zinc Telluride (CZT), etc. detector. A data acquisition electronics controller controls the data acquisition 124.

A cooling system 126 is configured to at least move air inside of the gantry 104 to remove heat away from temperature sensitive components. In one instance, the cooling system 126 includes a blower, a fan, etc. configured to draw ambient air into the gantry 104, e.g., into a plenum, and route the air to move heat away from temperature sensitive components. Hotter air inside of the gantry 104 moves outside of the gantry 104 via a blower, a fan, etc., convection, air pressure, etc. Additionally, a fan may be placed near a temperature sensitive component to draw air from the plenum and/or re-circulate air across or near a component to remove heat away from the component. A cooling system controller controls the cooling system 126.

Figures 2, 3, 4:
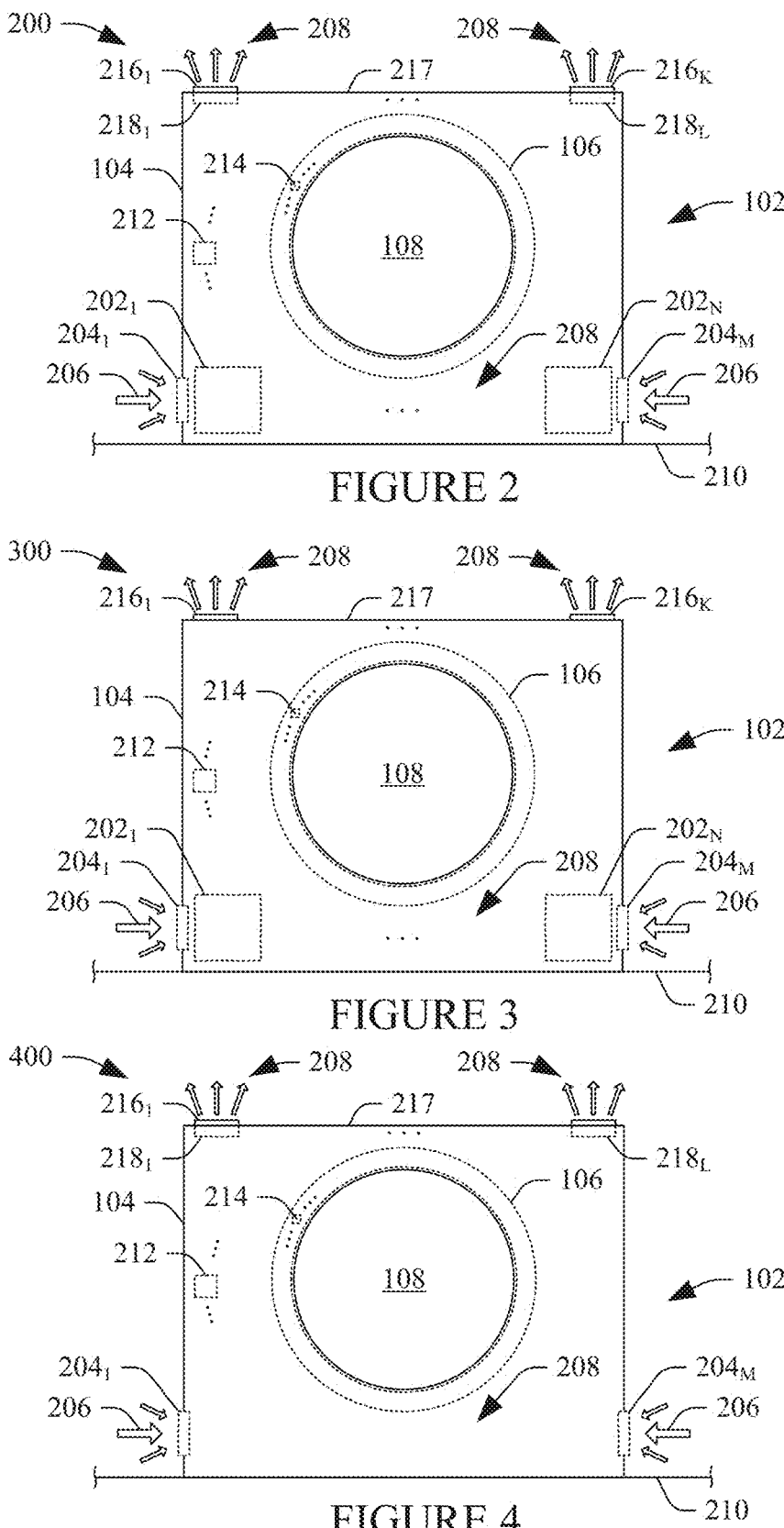
FIG. 2 schematically illustrates a non-limiting example of a portion of cooling system of the imaging system, in accordance with an embodiment(s) herein.
FIG. 3 schematically illustrates another non-limiting example of a portion of cooling system of the imaging system, in accordance with an embodiment(s) herein.
FIG. 4 schematically illustrates yet another non-limiting example of a portion of cooling system of the imaging system, in accordance with an embodiment(s) herein.

Briefly turning to FIGS. 2, 3 and 4, non-limiting examples of the cooling system 126 are schematically illustrated. Initially referring to FIG. 2, an example 200 of the cooling system 126 includes N intake blowers 202$_1$, . . . , and 202$_N$, where N in a positive integer equal to or greater than one. Collectively, the N intake blowers 202$_1$, . . . , and 202$_N$ are referred to herein as intake blowers 202. The example 200 further includes M intake vents 204$_1$, . . . , and 204$_M$, where M in a positive integer equal to or greater than one. Collectively, the M intake vents 204$_1$, . . . , and 204$_M$ are referred to herein as intake vents 204. In one instance, N=M. In another instance, N≠M.

The intake blowers 202 are disposed in the gantry 104 at locations at which the intake blowers 202 can draw ambient air 206 from outside of the gantry 104 into the gantry 106. In the illustrated example, the intake blowers 202 are disposed within a bottom region 208 of the gantry 104, which is supported by a floor 210 of an examination room in which the imaging system 102 resides. In other examples, at least one of the blowers 202 is disposed at a different location, including a location outside of the bottom region 208.

The example 200 further includes one or more air movers 212, e.g., a fan, etc. disposed in the gantry 104 and not on the rotating frame 106 and/or one or more air movers 214, e.g., a fan, etc. disposed in the gantry 104 on the rotating frame 106. At least one of the air movers 212 and/or 214 is disposed within a proximity of a temperature sensitive component at which the at least one of the air movers 212 and/or 214 can move air passed the temperature sensitive component, which, in one instance, facilitates moving hotter air away from the temperature sensitive component.

The example 200 further includes K exhaust vents 216$_1$, . . . , and 216$_K$, where K is a positive integer equal to or greater than one. Collectively, the K exhaust vents 216$_1$, . . . , and 216$_K$ are referred to herein as exhaust vents 216. The exhaust vents 216 are disposed in the gantry 104 at locations at which air can be expelled from the gantry 104 to the surrounding environment. In the illustrated example, the exhaust vents 216 are disposed in a top region 217 of the gantry 104. In other examples, at least one of the exhaust vents 216 is disposed at a different location, including a location outside of the top region 217.

The example 200 further includes L exhaust fans 218$_1$, . . . , and 218$_L$, where L is a positive integer equal to or greater than one. Collectively, the L exhaust fans 218$_1$, . . . , and 218$_L$ are referred to herein as exhaust fans 218. The exhaust fans 218 are disposed in the gantry 104 at locations at which the exhaust fans 218 can expel air from inside the gantry 104, through the exhaust vents 216, to outside of the gantry 104. In the illustrated example, the exhaust fans 218 are disposed directly below the exhaust vents 216. In other examples, at least one of the exhaust fans 218 is disposed at a different location, including not directly below an exhaust vent of the exhaust vents 216.

Moving to FIG. 3, an example 300 of the suitable cooling system 126 is substantially similar to the example 200 of the cooling system 126 described in connection with FIG. 2. For sake or brevity and clarity, only a difference(s) between the example 300 of the cooling system 126 and the example 200 of the cooling system 126 is described in connection with FIG. 3. In the example 300, all (as illustrated) or at least some (i.e., not all) of the exhaust fans 218 (FIGS. 2 and 4) are omitted.

Moving to FIG. 4, an example 400 of the suitable cooling system 126 is substantially similar to the example 200 of the cooling system 126 described in connection with FIG. 2. For sake or brevity and clarity, only a difference(s) between the example 400 of the cooling system 126 and the example 200 of the cooling system 126 is described in connection with FIG. 4. In the example 400, all (as illustrated) or at least some (i.e., not all) of the intake blowers 202 (FIGS. 2 and 3) are omitted.

Another example includes a combination of the example 300 of the cooling system 126 described in connection with FIG. 3 and the example 400 of the cooling system 126 described in connection with FIG. 4. Other examples are also contemplated herein. For example, another example additionally, or alternatively, includes a fluid cooling system. In yet another example includes an air cooling system, a fluid cooling system, and/or other cooling system.

Further examples of suitable cooling systems are described in U.S. Pat. No. 6,909,775 B2 to Ray et al., filed Dec. 16, 2002 and entitled "Computed tomography gantry cooling systems and methods," U.S. Pat. No. 7,065,173 B2 to Lacey et al., filed Dec. 2, 2003 and entitled "Method and apparatus for thermal management of CT electronics," and U.S. Pat. No. 7,236,562 B2 to Joshi et al., filed Nov. 3, 2005 and entitled "Method of assembly and thermal management of CT detector electronics circuits," all of which are incorporated herein in their entireties by reference. Other cooling systems are contemplated herein. In one instance, the cooling system 126 further includes a liquid cooling system.

Figures 5, 6, 7:
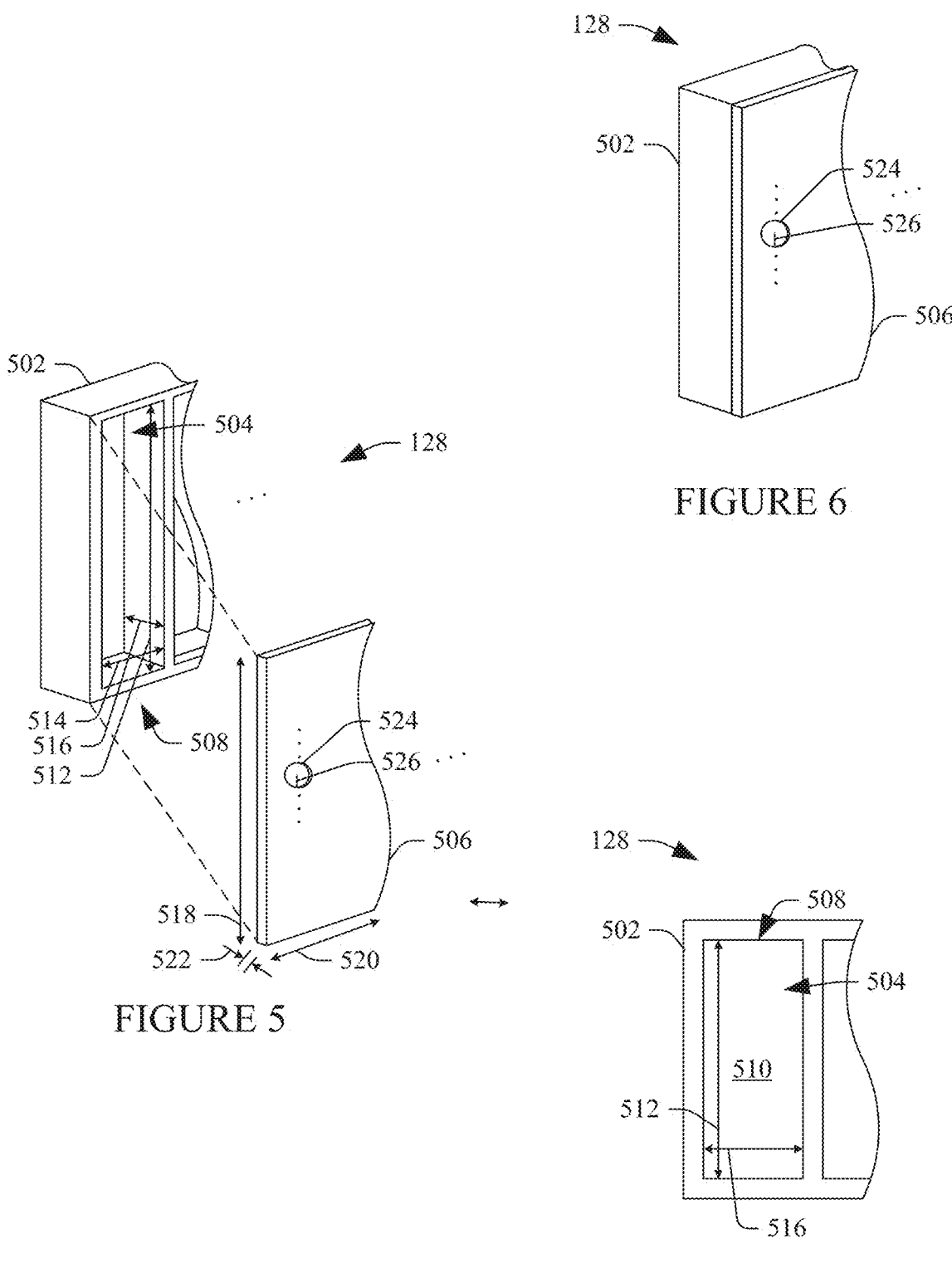
FIG. 5 schematically illustrates a non-limiting example of an exploded perspective view of a resonator of the portion of the cooling system of the imaging system, in accordance with an embodiment(s) herein.
FIG. 6 schematically illustrates a non-limiting example of a perspective view of a resonator of the portion of the cooling system of the imaging system, in accordance with an embodiment(s) herein.
FIG. 7 schematically illustrates a non-limiting example of a front view of a chamber of the resonator of the portion of the cooling system of the imaging system, in accordance with an embodiment(s) herein.

Returning to FIG. 1, an audible noise reducer 128 is configured to reduce audible noise (i.e., unintended and/or undesired sound) produced by a component of the imaging system 102, e.g., by the cooling system 126, the rotating frame 106, etc. FIGS. 5, 6 and 7 schematically illustrates an example of a portion of the audible noise reducer 128. FIG. 5 schematically illustrates an exploded perspective view, FIG. 6 schematically illustrates a perspective view, and FIG. 7 schematically illustrates a font view of part of the portion of the audible noise reducer 128.

With reference to FIGS. 5, 6 and 7, the audible noise reducer 128 includes at least one resonator 502. The resonator 502 includes at least one chamber 504 with an open side 508 and a cover 506 disposed over the open side 508. The chamber 504 includes a plurality of walls arranged with respect to each other to from a rectangular box (i.e., a cuboid) enclosing a cavity 510. The cavity 510 has a length 512, a width 514 and a depth 516. The cover 506 has a length 518, a width 520 and a depth 522. The cover 506 further includes at least one aperture 524 having a depth equal to the depth 522 of the cover 506 and a radius 526. The at least one aperture 524 provides a material free region between the cavity 510 and an environment outside of the audible noise reducer 128, allowing sound to travel between the cavity 510 and the environment.

The resonator 502 is configured to resonate at a predetermined frequency corresponding to audible noise of interest, e.g., a frequency of sound from the intake blowers 202 (FIGS. 2, 3 and 4), a frequency of sound from the rotating frame 106 (FIGS. 2, 3 and 4), etc. For example, in one instance the dimensions of the cavity 510 and the aperture 524 are based on the principle of Helmholtz resonance, as shown in EQUATION 1:

$$f_0 = \frac{c}{2\pi}\sqrt{\frac{A}{VL}}, \qquad \text{EQUATION 1}$$

where $f_0$ represents the resonant/natural frequency of interest of the audible noise to be removed, c represents the speed of sounds, A represents a cross-sectional area (i.e., $2\pi r^2$) of the aperture 524, V represents a volume (i.e., l×w×d) of the cavity 510, and L represents the depth 522 (i.e., d) of the aperture 524. Sound waves passing out of the resonator 504 are out of phase with the frequency of the audible noise of interest and destructively interfere with the frequency of the audible noise of interest.

The audible noise of interest can be variously determined. For example, in one instance the imaging system 102 can be operated and sound from the intake blowers 202 (FIGS. 2, 3 and 4) while blowing, the rotating frame 106 (FIGS. 2, 3 and 4) while rotating, etc. can be recorded and spectrally analyzed. In another instance, the imaging system 102 can be operated with the intake blowers 202 (FIGS. 2, 3 and 4) blowing while the rotating frame 106 (FIGS. 2, 3 and 4) is parked at a static position, etc. and the sound of the blowers 202 (FIGS. 2, 3 and 4) can be recorded and spectrally analyzed, and/or with the rotating frame 106 rotating while the intake blowers 202 are turned off. In yet another instance, manufacturer specifications for the intake blowers 202 (FIGS. 2, 3 and 4), etc. are utilized to determine the audible noise of interest, where such information is available.

In FIGS. 5, 6 and 7, the cavity 510 has a cuboidal shape and the at least one aperture 524 has a circular cylindrical shape. In other embodiments, the cavity 510 is otherwise shaped, e.g., a polyhedron other than rectangular, a spherical shape, an ellipsoidal shape, a cylindrical shape, etc., and/or the at least one aperture 524 is otherwise shaped, e.g., a cube, a cuboidal, an elliptic cylinder, etc. In FIGS. 5, 6 and 7, the resonator 502 is described in connection with the at least one chamber 508. With configurations including more than one chamber 508, the chambers 508 and/or respective apertures 524 can have the same dimensions, shapes, etc. or at least one of the chambers 508 and/or apertures 524 can have a different dimension. As such, the resonator 502 can be tuned to cancel more than one frequency of audible noise.

As described in greater detail below, in one instance the at least one resonator 502 is located in connection with the imaging system 102 to receive the audible noise of interest. With this configuration, received audible noise of interest results in the resonator 502 resonating at the natural frequency of audible noise of interest and emitting sound waves that destructively interfere with and cancel at least some of the audible noise of interest, reducing the audible noise of interest. In one instance, the approach described herein can reduce the audible noise that can be audibly perceived by the subject and/or the clinician, e.g., lower frequency audible noise from blowers and/or fans of the imaging system 102. This may allow for further increasing blower and/or fan speed, providing additional cooling, while maintaining or reducing a level of the audible noise of interest.

Returning to FIG. 1, a subject/object support 130 includes a tabletop 132 moveably coupled to a frame/base 134. In one instance, the tabletop 132 is slidably coupled to the frame/base 134 via a bearing or the like, and a drive system (not visible) including a controller, a motor, a lead screw, and a nut (or other drive system) translates the tabletop 132 along the frame/base 134 into and out of the examination region 108. The tabletop 132 is configured to support an object or subject in the examination region 108 for loading, scanning, and/or unloading the subject or object. A table controller controls the drive system.

For a helical scan, the rotating frame 106 rotates in coordination with the tabletop 132 moving along the Z-axis 110, and active detector elements of the radiation sensitive detector 124 detect radiation over consecutive arc segments (integration periods) each revolution and generate respective signals. For an axial (step and shoot) scan, the tabletop 132 is positioned at a static position for each integration period and moves between integration periods. For each arc segment, the data acquisition electronics 124 processes each signal and generates projection data.

A reconstructor 136 reconstructs the projection data and generates volumetric (3-D) image data for a helical scan and/or individual axial (2-D) images for an axial step and shoot scan (which can be used in combination to generate volumetric image data). The volumetric image data and/or 2-D slices thereof, and/or the individual axial images can be visually presented, filmed, etc. Examples of suitable reconstruction algorithms include filtered back projection (FBP), advanced statistical iterative reconstruction (ASIR), conjugate gradient (CG), maximum likelihood expectation maximization (MLEM), model-based iterative reconstruction (MBIR), and/or other reconstruction algorithm.

A computing system 138 serves as an operator console of the system 102. The computing system 138 may include a computer, a workstation, etc. The computing system 138 includes input/output (I/O) 140. An input device 142 includes a keyboard, mouse, touchscreen, microphone, etc. The input device 142 is in electrical communication with the computing system 138 through the I/O 140 and/or otherwise. An output device 144 includes a human readable device such as a display monitor or the like. The output device 144 is in electrical communication with the computing system 138 through the I/O 140 and/or otherwise.

A remote resource 146 includes one or more of a server, a workstation, a Radiology Information System (RIS), a Hospital Information System (HIS), an electronic medical record (EMR), a Picture Archiving and Communications System (PACS), one or more other CT scanners, cloud processing resources (which includes shared remote data storage and/or computing power, including processing resources distributed over multiple locations/data centers), etc. The remote resource 146 is in electrical communication with the computing system 138 through the I/O 140 and/or otherwise.

The computing system 138 further includes a processor(s) 148 such as a microprocessor (μP), a central processing unit (CPU), graphics processing unit (GPU), etc., and computer readable medium 150, which includes non-transitory medium and excludes transitory medium (signals, carrier waves, and the like). The computer readable medium 150 is embedded or encoded with computer executable instructions, e.g., application software, which allows a user to select a protocol, start scanning, etc.

Figure 8:
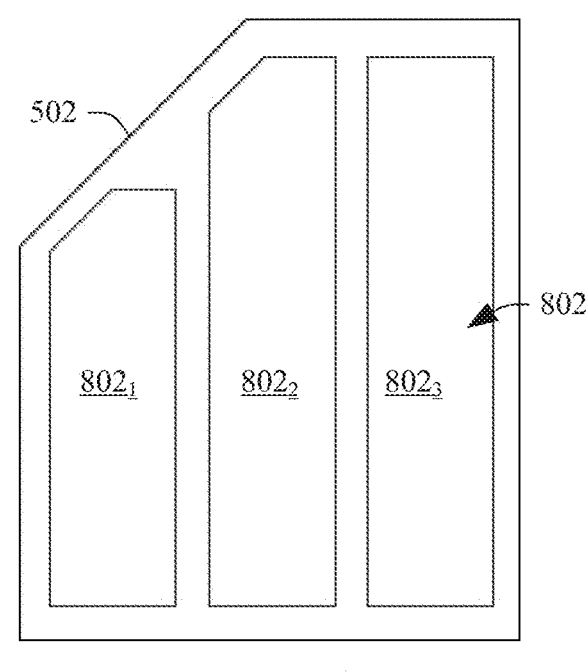
FIG. 8 schematically illustrates a non-limiting example of a front view of the resonator configured with three chambers, in accordance with an embodiment(s) herein.
Figure 9:
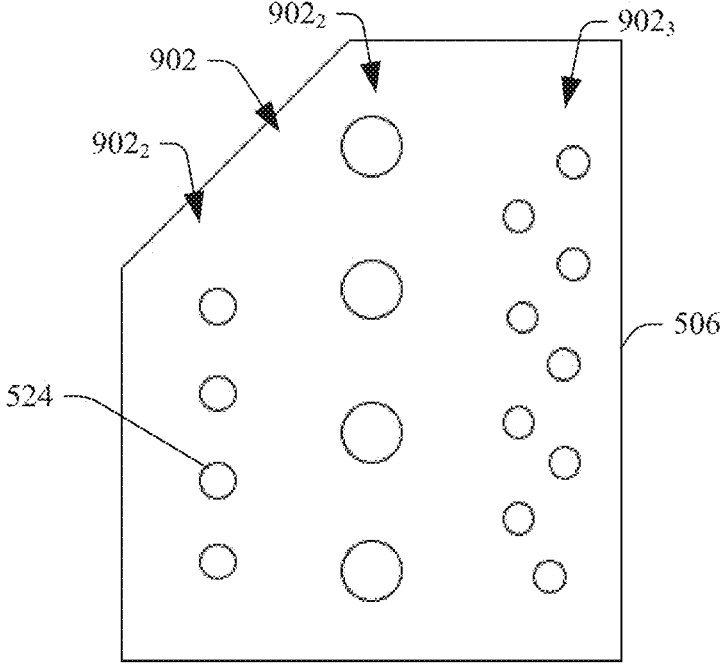
FIG. 9 schematically illustrates a non-limiting example of a cover of the resonator configured with three sets of apertures, in accordance with an embodiment(s) herein.

FIG. 8 schematically illustrates another non-limiting example of the resonator 502. In this example, the resonator 502 includes three (3) chambers 802₁, 802₂ and 802₃, collectively referred to herein as chambers 802. The cover 506 includes three (3) sets 902₁, 902₂ and 902₃, of the at least one aperture 524, collectively referred to herein as sets 902 of the at least one aperture 524. The first set 902₁ of the at least one aperture 524 corresponds to the chamber 802₁, the second set 902₂ of the at least one aperture 524 corresponds to the chamber 802₂, and the third set 902₃ of the at least one aperture 524 corresponds to the chamber 802₃.

In this examples, the chambers 802 have different dimensions and/or shapes, and, hence, volumes. All of the sets 902 of the at least one aperture 524 do not have a same numbers of the at least one aperture 524, and the at least one aperture 524 of the sets 902 of have different dimensions, and, hence, cross-sectional area. As discussed herein, the dimensions of the chambers 802 (the volume) and the at least one aperture 524 of the sets 902 (at least the cross sectional area) determine the resonant frequencies of the resonator 502. In this example, the resonator 502 is configured to dampen the natural frequencies of three (3) different frequencies of interest of the audible noise.

As discussed herein, in one instance the at least one resonator 502 is located in connection with the imaging system 102 to receive the audible noise of interest. In one instance, the at least one resonator 502 is disposed inside of the gantry 104 (FIG. 1). In another instance, the at least one resonator 502 is disposed outside of the gantry 104 (FIG. 1). In yet another instance, the at least one resonator 502 is disposed partially inside and partially outside of the gantry 104 (FIG. 1). FIGS. 10, 11, 12 and 13 schematically illustrate a non-limiting example of the resonator 502 installed in the imaging system 102.

FIGS. 10, 11 and 12 schematically illustrate different perspective views of portions of covers of the gantry 104. FIG. 10 illustrates a view of the portion of a cover 1002 from the outside of the imaging system 102. FIG. 11 illustrates a view from inside of the portion of the cover 1002 from inside of the cover 1002. In this example, the resonator 502 is installed in the portion of the cover 1002. FIG. 12 illustrates a view from inside of a portion of a cover 1202 for the other side of the gantry 104. In this example, the resonator 502 is installed in the portion of the cover 1202.

FIG. 13 schematically illustrates the imaging system 102 with the portion of the cover 1002 described in connection with FIG. 10 installed on the gantry 104 described in connection with FIG. 2. In this example, the resonator 502 is disposed near the intake blower 202₂. In another example, the resonator 502 is otherwise located with respect to the intake blower 202₂, but is located in a vicinity in which the resonator 502 receives audible noise produced by the intake blower 202₂, e.g., from air flow and/or otherwise. In this instance, the resonator 502 can be located inside of the gantry 104 or outside of the gantry 104, e.g., in connection with a cover of the imaging system 102 or otherwise.

In FIG. 13, the resonator 502 is shown disposed in connection with the intake blower 202ₙ. In another example, more than one resonator 502 is disposed with the imaging system 102. For example, in one instance, multiple resonators 502 are disposed in connection with multiple intake blowers 202. In another instance, one or more resonators 502 are disposed, additionally or alternatively, in connection one or more of the exhaust fans 218. In another instance, one or more resonators 502 are disposed, additionally or alternatively, in connection another component of the imaging system 102.

FIGS. 14, 15, 16, 17, 18 and 19 schematically illustrate a self-tuning variation of the resonator 502. In general, the self-tuning resonator 502 is configured to resonate, alternatively, at one of at least two predetermined frequencies. A first of the at least two predetermined frequencies corresponds to a first air flow across the resonator 502, and a second of the at least two predetermined frequencies corresponds to a second air flow across the resonator 502, where the second air flow is greater than the first air flow. The default position of the resonator corresponds to the first frequency, and the resonator 502 automatically adjusts to second position corresponding to the second frequency in response to a change in the air flow speed (i.e., a speed of an intake blower, a speed of a fan, the rotational speed of the rotating frame 106, etc.).

Figure 14:
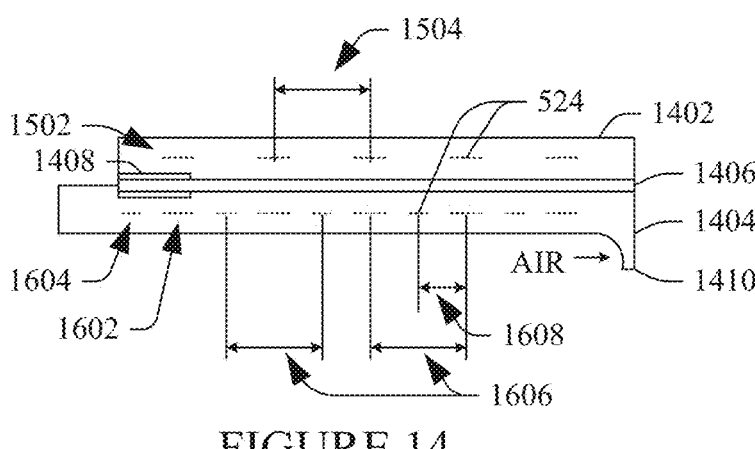
FIG. 14 schematically illustrates a top down view of the self-tuning resonator with the second plate installed on the first plate and at a default position, in accordance with an embodiment(s) herein.

FIG. 14 schematically illustrates a top down view of the self-tuning resonator 502. In this example, the resonator 502 includes a first plate 1402 and a second plate 1404. The second plate 1404 is moveably disposed relative to the first plate 1402 via bearing 1406 or the like. For example, in one instance the first plate 1402 and the second plate 1404 respectively include complementary sides of a linear slide, a ball bearing slide, a plain bearing slide, a roller slide, a magnetic slide, etc. It is to be appreciated that the size, location, shape, etc. of the bearing 1406 is for explanatory purposes and is non-limiting.

An elastic member 1408 is affixed to both the first plate 1402 and the second plate 1404. The elastic member 1408 is configured to maintain the position of the second plate 1404 relative to the first plate 1402 until a change in air flow speed to an air flow speed corresponding to the second frequency. An example of the elastic member 1408 is a preloaded spring, configured to operate with a tension load where the spring stretches in response to a certain load from the air flow or with a compression load where the spring compresses in response to a certain load from the air flow, depending on where the elastic member 1408 is attached to the first plate 1402 and the second plate 1404. It is to be appreciated that the size, location, shape, etc. of the elastic member 1408 is for explanatory purposes and is non-limiting.

The second plate 1404 is configured to move across the first plate 1402 between at least the default position corresponding to the first frequency and the second position corresponding to the second frequency. The example second plate 1404 further includes a protrusion 1410 extending in a direction opposite of the position of the first plate 1402 and out of the second plate 1404. At least some of the air flow flowing across the second plate 1404 impinges and exerts a force on the protrusion 1410, urging the second plate 1404 to move in the direction of the air flow. In another instance, the protrusion 1410 is omitted and/or a different type of air catch is employed.

Figure 15:
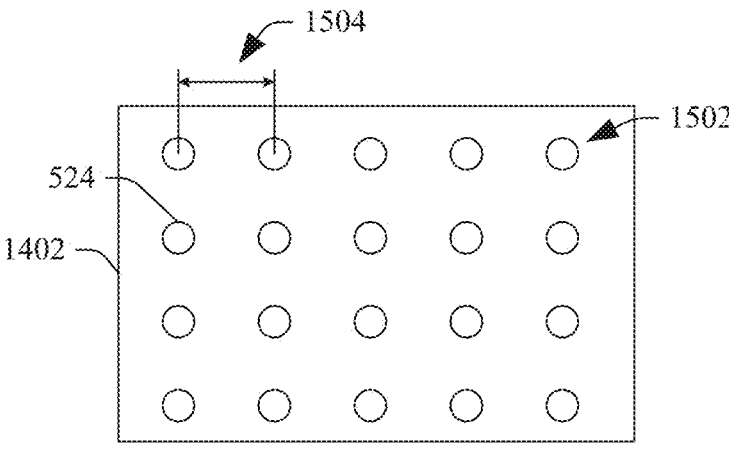
FIG. 15 schematically illustrates a front view of a first plate of the self-tuning resonator, in accordance with an embodiment(s) herein.
Figure 16:
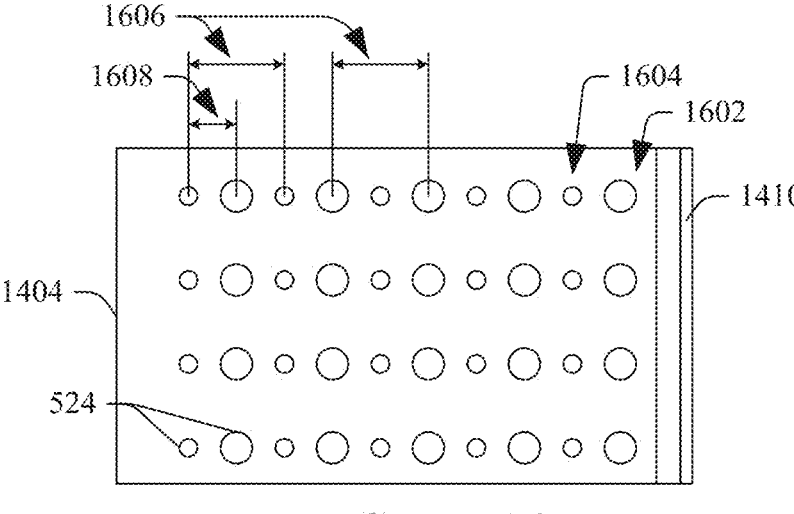
FIG. 16 schematically illustrates a front view of a second plate of the self-tuning resonator, in accordance with an embodiment(s) herein.

FIG. 15 schematically illustrates a front view of the first plate 1402, and FIG. 16 schematically illustrates a front view of the second plate 1404. With reference to FIGS. 14 and 15, the first plate includes a first 1502 set of first size apertures 524. A pitch 1504 between centers of neighboring apertures 524 is a first distance. With reference to FIGS. 14 and 16, the second plate includes a first set 1602 of the first size apertures 524 and a second set 1604 of second different size apertures 524. A pitch 1606 between centers of adjacent same size apertures 524 is the first distance, and a pitch 1608 between centers of neighboring different size apertures 524 is a second different distance, which is approximately half of the first distance.

Figure 17:
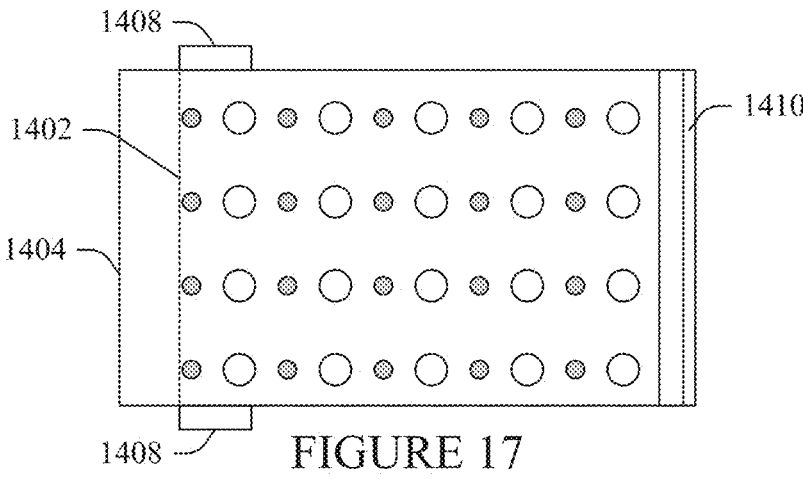
FIG. 17 schematically illustrates a front view of the second plate of the self-tuning resonator installed on the first plate of the self-tuning resonator at the default position, in accordance with an embodiment(s) herein.

FIG. 17 schematically illustrates a front view of the second plate 1404 installed on the first plate 1402 at the default position. With reference to FIGS. 14 and 17, in the default position, the first plate 1402 and the second plate 1404 are arranged such that the apertures 524 of the first set 1602 of the second plate 1404 spatially align with the apertures 524 of the first set 1502 of the first plate 1402, and the apertures 524 of the second set 1604 of the second plate 1404 are disposed over portions of the first plate 1402. In FIG. 17, gray shading is utilized to illustrate the apertures 524 of the second set 1604 of the second plate 1404 that are disposed over portions of the first plate 1402, and no shading is utilized to illustrate the apertures 524 of the first set 1602 of the second plate 1404 that spatially align with the apertures 524 of the first set 1502 of the first plate 1402.

Figure 18:
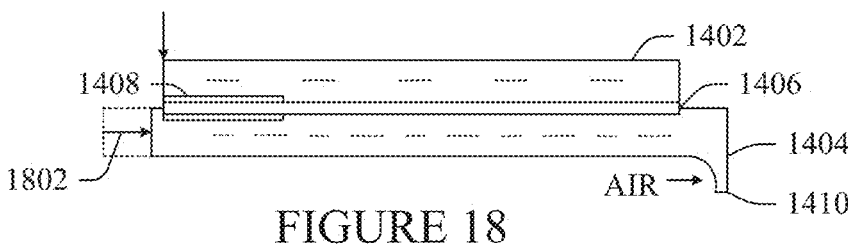
FIG. 18 schematically illustrates a top down view of the self-tuning resonator with the second plate installed on the first plate and at a second position, in accordance with an embodiment(s) herein.
Figure 19:
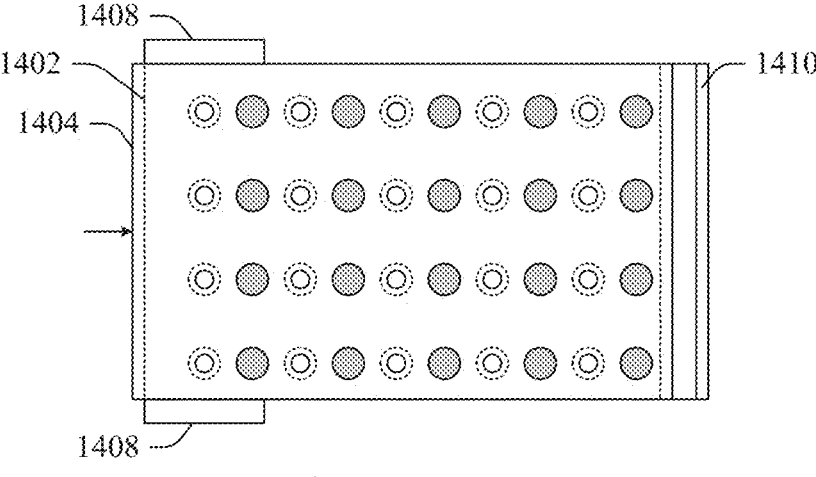
FIG. 19 schematically illustrates a front view of the second plate of the self-tuning resonator installed on the first plate of the self-tuning resonator at the second position, in accordance with an embodiment(s) herein.

FIG. 18 schematically illustrates a top down view of the self-tuning resonator 502 with the second plate 1404 at the second position. In this example, the air flow across the second plate 1404 resulted in a displacement 1802 of the second plate 1404, which resulted in movement of the second plate 1404 across the first plate 1402 via the bearing 1406 from the default position corresponding to the first frequency to the second position corresponding to the second frequency. FIG. 19 schematically illustrates a front view of the second plate 1404 on the first plate 1402 at the second position.

With reference to FIGS. 18 and 19, in the second position, the first plate 1402 and the second plate 1404 are arranged such that the apertures 524 of the second set 1604 of the second plate 1404 spatially align with the apertures 524 of the first set 1502 of the first plate 1402, and the apertures 524 of the first set 1602 of the second plate 1404 are disposed over portions of the first plate 1402. In FIG. 19, gray shading is utilized to illustrate the apertures 524 of the first set 1602 of the second plate 1404 that are disposed over portions of the first plate 1402, and no shading is utilized to illustrate the apertures 524 of the second set 1604 of the second plate 1404 that spatially align with the apertures 524 of the first set 1502 of the first plate 1402.

In operation, the first plate 1402 and the second plate 1404 are initially aligned as illustrated in FIGS. 14 and 17 where the apertures 524 of the first set 1602 of the second plate 1404 spatially align with the apertures 524 of the first set 1502 of the first plate 1402, and the apertures 524 of the second set 1604 of the second plate 1404 are disposed over portions of the first plate 1402. As discussed herein, the elastic member 1408 maintains the first plate 1402 and the second plate 1404 at the default position and allows the second plate 1404 to move across the first plate 1402 when air flow surpasses a predetermined air flow speed threshold, which urges the second plate 1404 to move.

In one instance, initially, there is no air flow across the second plate 1404. For example, the intake blowers 202, the air movers 214, the rotating frame 106, etc. may not be blowing and/or rotating. In another instance, initially, there is air flow across the second plate 1404, but the air flow is not enough to move the second plate 1404. In these instances, the resonator 502 is tuned to cancel the first frequency. If the air flow increases to a point where it overcomes the pre-loading of the elastic member 1408, the second plate 1404 slides across the first plate 1402 to the second position such that the apertures 524 of the second set 1604 of the second plate 1404 spatially align with the apertures 524 of the first set 1502 of the first plate 1402. At this position, the resonator 502 is tuned to cancel the second frequency.

Should the air flow decrease to a point where it no longer overcomes the pre-loading of the elastic member 1408, the second plate 1404 slides across the first plate 1402 to the default position where the apertures 524 of the first set 1602 of the second plate 1404 spatially align with the apertures 524 of the first set 1502 of the first plate 1402. At this position, the resonator 502 is tuned to cancel the first frequency. In another instance, initially, there is enough air flowing across the second plate 1404 that the second plate 1404 is at the second position where the apertures 524 of the second set 1604 of the second plate 1404 spatially align with the apertures 524 of the first set 1502 of the first plate 1402.

In FIGS. 14, 15, 16, 17, 18 and 19, a combination of the bearing 1406 and the elastic member 1408 are utilized to provide movement of the second plate 1404 relative to the first plate 1402 between the default position and the second position. In a variation, an actuator is utilized to move the second plate 1404. In another variation, where the resonator 502 is disposed on a rotating member such as the rotating frame 106, centrifugal force can be utilized to move the second plate 1404 relative to the first plate 1402 between the default position and the second position. In another variation, the second plate 1404 has N different size apertures 524, each corresponding to a different frequency of interest, and N different flows result respectively result in the second plate 1404 moving to the N different positions.

Figure 20:
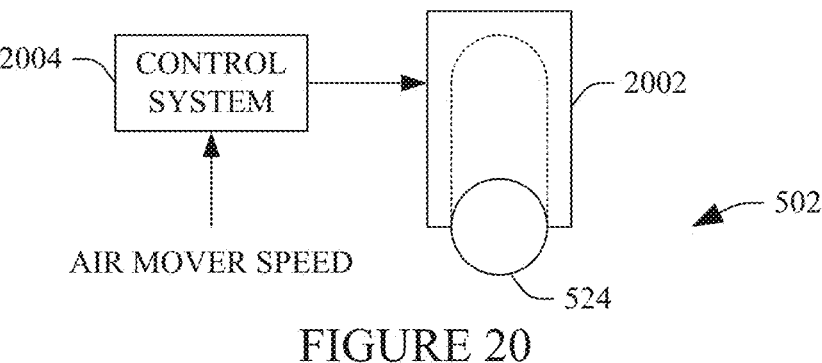
FIG. 20 schematically illustrates an example of an electromechanically controlled aperture of the resonator at a first position with a first size aperture, in accordance with an embodiment(s) herein.
Figure 21:
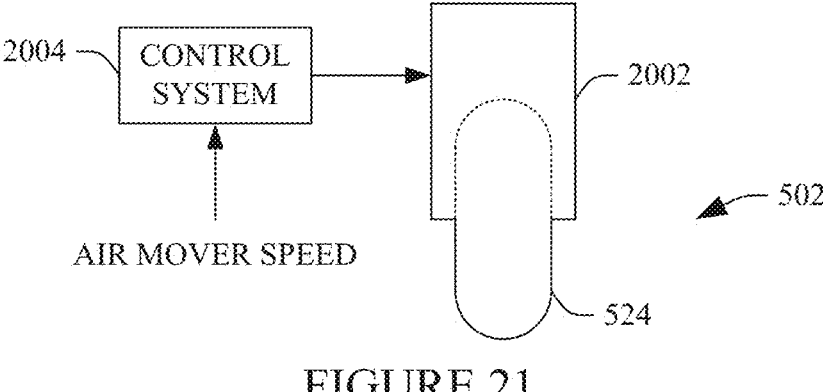
FIG. 21 schematically illustrates an example of the electromechanically controlled aperture of the resonator at an Ith position with an Ith size aperture, in accordance with an embodiment(s) herein.
Figure 22:
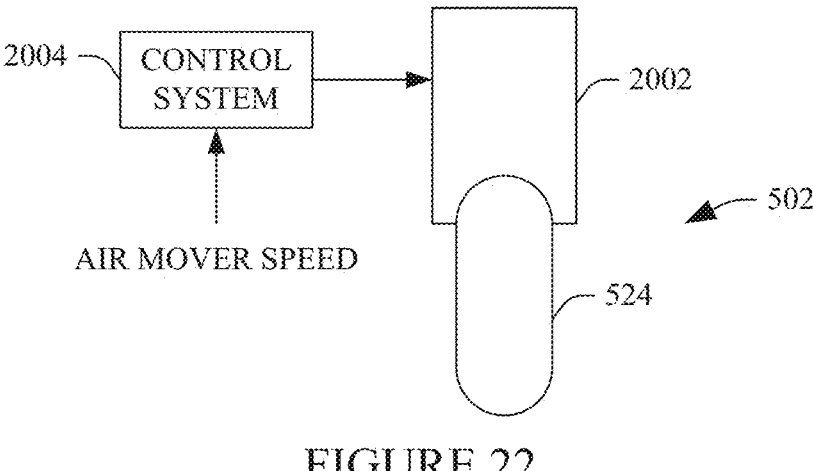
FIG. 22 schematically illustrates an example of the electromechanically controlled aperture of the resonator at an Nth position with an Nth size aperture, in accordance with an embodiment(s) herein.

In FIGS. 14, 15, 16, 17, 18 and 19, the resonator 502 is self-tuning in that the second plate 1404 automatically adjusts its position based on air flow to cancel sound at the prevalent frequency, the first frequency or the second frequency. FIGS. 20, 21 and 22 schematically illustrate a variation in which a size of the apertures 524 is electromechanically controlled. FIGS. 20, 21 and 22 schematically illustrate a single aperture 524 of the resonator 502 in connection with a collimating device 2002 and a controller control system 2004.

In one instance, the collimating device 2002 is disposed in connection with the cover 506 via a linear slide, a ball bearing slide, a plain bearing slide, a roller slide, a magnetic slide, etc. In one instance, the collimating device 2002 is configured to move between a plurality of predetermined positions, including a first position (FIG. 20) at which the single aperture 524 is a first size, through an Ith position (FIG. 21) at which the single aperture 524 is an Ith size, to an Nth position (FIG. 22) at which the single aperture 524 is an Nth size, where N is an integer greater than one.

In FIGS. 20, 21 and 22, each of the positions corresponds to a different size aperture 524 for a given chamber 508 and, hence, a different frequency of interest (that corresponds to an audible noise) to cancel. In FIG. 20, the size of the aperture is smaller than the size of the aperture in FIGS. 21 and 22, and the size of the aperture in FIG. 21 is smaller than the size of the aperture in FIG. 22. With this configuration, the resonator 502 is configured for N different frequencies, with the current frequency of interest depending on the current location of the collimating device 2002 with respect to the aperture 524.

The control system 2004, in one instance, includes a controller, a motor, a drive, an encoder, etc. The control system 2004 is programmed with a look-up table (LUT), a data structure, a database, etc. with a mapping between an intake blower/air mover speed and a position of the collimating device 2002 relative to the aperture 524, and, hence, a specific frequency of interest to cancel. The control system 2004 receives the intake blower/air mover speed and controls the components therein based on the received intake blower/air mover speed to move the collimating device 2002 to adjust the size of the aperture 524.

In one instance, the intake blower/air mover speed is provided to the control system 2004 via the operator console 138 (FIG. 1), e.g., a numerical value indicating a voltage being applied to the intake blower/air mover. In another instance, the intake blower/air mover speed is obtained from the intake blower/air mover, e.g., via the voltage being applied to the intake blower/air mover. In other instance, 2004 or intake blower/air mover speed is provided to the control system 2004 otherwise.

Figures 23, 24:
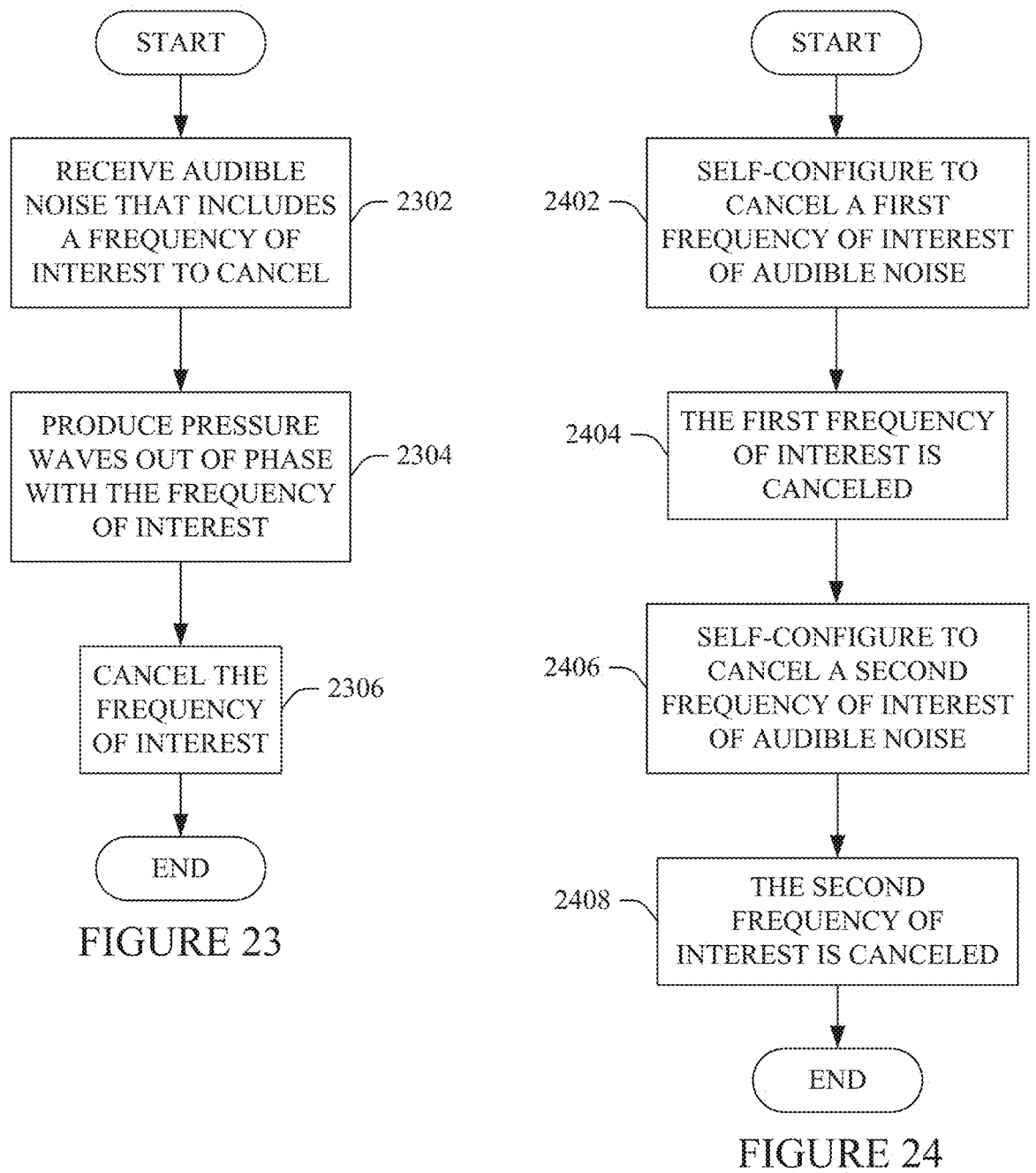
FIG. 23 illustrates an example of a flow chart for a computer-implemented method, in accordance with an embodiment(s) herein.
FIG. 24 illustrates an example of a flow chart for another computer-implemented method, in accordance with an embodiment(s) herein.

FIG. 23 illustrates non-limiting examples of a flow chart for a computer-implemented method for reducing audio noise in connection with an imaging system. It is to be appreciated that the ordering of the acts in one or more of the methods is not limiting. As such, other orderings are contemplated herein. In addition, one or more acts may be omitted, and/or one or more additional acts may be included.

At 2302, the resonator 502, tuned to cancel at least one frequency of interest corresponding to audible noise, receives the audible noise produced by a component of the imaging system 102, as described herein and/or otherwise. At 2304, the resonator 502, in response thereto, resonates at the frequency of interest and produces pressure waves at the frequency of interest that are out of phase with the received frequency of interest, as described herein and/or otherwise.

At 2306, the pressure waves produced by the resonator 502 destructively interfere with the pressure waves produced by the component, canceling the frequency of interest corresponding to audible noise, and, hence, the audible noise, as described herein and/or otherwise. As discussed herein, this allows for reducing a level of the audible noise that can be audibly perceived by a subject being imaged and/or a clinician operating the CT imaging system for an imaging examination of the subject, which also allows for increasing blower and/or fan speed, providing further cooling for the system, which can improve system performance.

FIG. 24 illustrates another non-limiting examples of a flow chart for a computer-implemented method for reducing audio noise in connection with an imaging system. It is to be appreciated that the ordering of the acts in one or more of the methods is not limiting. As such, other orderings are contemplated herein. In addition, one or more acts may be omitted, and/or one or more additional acts may be included.

At 2402, first air flow across the resonator 502 self-configures the resonator 502 to cancel a first frequency of interest of audible noise, as described herein and/or otherwise. At 2404, the first frequency of interest is canceled, as described herein and/or otherwise. At 2406, a second different air flow across the resonator 502 self-configures resonator 502 to cancel a second frequency of interest of audible noise, as described herein and/or otherwise.

At 2408, the second frequency of interest is canceled, as described herein and/or otherwise. As discussed herein, this allows for reducing a level of the audible noise that can be audibly perceived by a subject being imaged and/or a clinician operating the CT imaging system for an imaging examination of the subject, which also allows for increasing blower and/or fan speed, providing further cooling for the system, which can improve system performance.

Figures 25, 26:
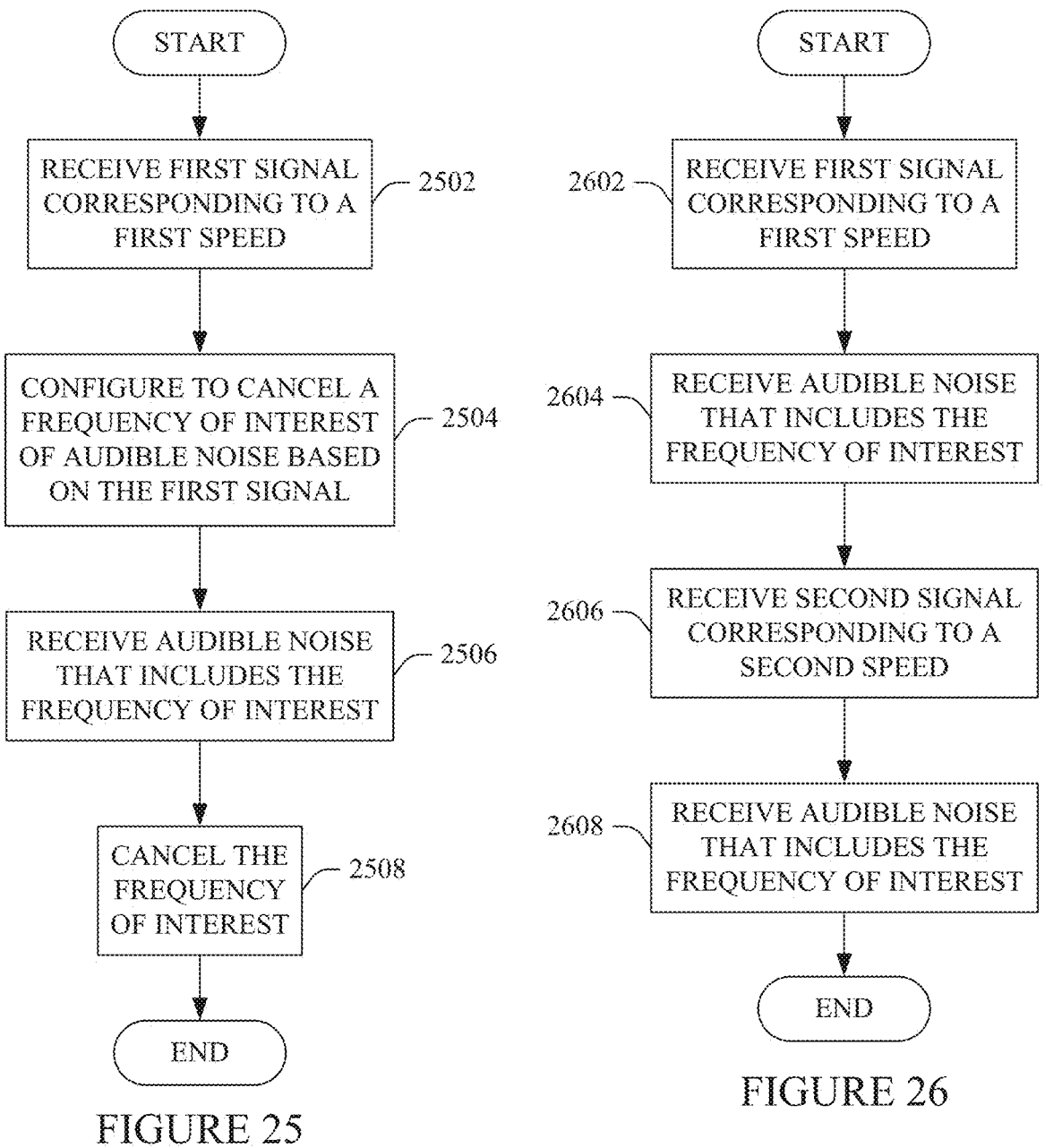
FIG. 25 illustrates an example of a flow chart for yet another computer-implemented method, in accordance with an embodiment(s) herein.
FIG. 26 illustrates another example of a flow chart for still another computer-implemented method, in accordance with an embodiment(s) herein.

FIG. 25 illustrates another non-limiting examples of a flow chart for a computer-implemented method for reducing audio noise in connection with an imaging system. It is to be appreciated that the ordering of the acts in one or more of the methods is not limiting. As such, other orderings are contemplated herein. In addition, one or more acts may be omitted, and/or one or more additional acts may be included.

At 2502, the resonator 502 receives a first signal corresponding to a first speed of a moving component, as described herein and/or otherwise. At 2504, the resonator 502 is configured to cancel a frequency of audible noise produced by the moving component based on the first signal, as described herein and/or otherwise. At 2506, the resonator 502 receives the audible noise produced by the moving component, as described herein and/or otherwise.

At 2508, the second frequency of interest is canceled, as described herein and/or otherwise. As discussed herein, this allows for reducing a level of the audible noise that can be audibly perceived by a subject being imaged and/or a clinician operating the CT imaging system for an imaging examination of the subject, which also allows for increasing blower and/or fan speed, providing further cooling for the system, which can improve system performance.

FIG. 26 illustrates another non-limiting examples of a flow chart for a computer-implemented method for reducing audio noise in connection with an imaging system. It is to be appreciated that the ordering of the acts in one or more of the methods is not limiting. As such, other orderings are contemplated herein. In addition, one or more acts may be omitted, and/or one or more additional acts may be included.

At 2602, the resonator 502 is configured to cancel a first frequency of interest of audible noise produced by the moving component based on a first signal provided to the resonator, as described herein and/or otherwise. At 2604, the resonator 502 receives the audible noise and cancels the first frequency of interest, as described herein and/or otherwise. At 2606, the resonator 502 is configured to cancel a second frequency of interest of the audible noise produced by the moving component based on a second signal provided to the resonator, as described herein and/or otherwise.

At 2608, the resonator 502 receives the audible noise and cancels the second frequency of interest, as described herein and/or otherwise. As discussed herein, this allows for reducing a level of the audible noise that can be audibly perceived by a subject being imaged and/or a clinician operating the CT imaging system for an imaging examination of the subject, which also allows for increasing blower and/or fan speed, providing further cooling for the system, which can improve system performance.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspects. Similarly, features set forth in dependent claims can be combined with non-mutually exclusive features of other dependent claims, particularly where the dependent claims depend on the same independent claim. Single claim dependencies may have been used as practice in some jurisdictions that require them, but this should not be taken to mean that the features in the dependent claims are mutually exclusive.

What is claimed is:

1. A computed tomography imaging system, comprising:
   a gantry;
   a rotating frame rotatably supported in the gantry, the rotating frame, including:
      an X-ray source configured to emit X-ray radiation that traverses an examination region; and
      an X-ray radiation sensitive detector disposed opposite the X-ray source across the examination region and configured to detect X-ray radiation traversing the examination region and generate a signal indicative of the detected X-ray radiation;
   at least one component of the gantry or the rotating frame that produces audible noise; and
   an audible noise reducer configured to reduce the audible noise, wherein the audible noise reducer includes a resonator tuned to a first frequency of the audible noise.

2. The computed tomography imaging system of claim 1, wherein the resonator includes a first chamber and a cover with a first region for the first chamber that includes a first set of apertures, a first volume of the first chamber and a first cross-sectional area and a first depth of the apertures of the first set correspond to the first frequency, and the resonator resonates at the first frequency in response to receiving the audible noise.

3. The computed tomography imaging system of claim 2, wherein the resonator includes a second chamber and the cover includes a second region for the second chamber that includes a second set of apertures, and a second volume of the second chamber and a second cross-sectional area and a second depth of the apertures of the second set correspond to the second frequency.

4. The computed tomography imaging system of claim 3, wherein the resonator concurrently reduces the first frequency and the second frequency.

5. The computed tomography imaging system of claim 1, wherein the resonator includes a first chamber and a cover with a first region for the first chamber that includes a first set of adjustable size apertures, wherein a first size of the apertures correspond to first frequency and a second size of the apertures correspond to a second frequency of the audible noise.

6. The computed tomography imaging system of claim 5, wherein the resonator alternatively reduces the first frequency and the second frequency.

7. The computed tomography imaging system of claim 6, further including:

a controller configured to control a size of the apertures.

8. The computed tomography imaging system of claim 6, wherein the resonator is configured to automatically switch between reducing the first frequency and reducing the second frequency based on a speed of air flow across resonator.

9. The computed tomography imaging system of claim 1, further including:

a gantry cover, wherein the gantry cover includes the resonator.

10. The computed tomography imaging system of claim 1, wherein the at least one component includes at least one of an intake blower and a fan.

11. The computed tomography imaging system of claim 1, wherein the at least one component includes the rotating frame.

12. A method, comprising:

receiving audible noise at a resonator of an imaging system, wherein the audible noise is produced by a component of the imaging system, and the resonator is tuned to a first frequency of the audible noise, wherein the resonator includes a first chamber and a cover with a first region for the first chamber that includes a first set of apertures, a first volume of the first chamber and a first cross-sectional area and a first depth of the apertures of the first set correspond to the first frequency; and generating, by the resonator, an audible signal at the first frequency and out of phase of the first frequency, wherein the generated signal destructively interferes with the first frequency, thereby reducing the audible noise.

13. The method of claim 12, wherein the resonator is tuned to at least a second frequency of the audible noise, the resonator includes a second chamber and the cover includes a second region for the second chamber that includes a second set of apertures, and a second volume of the second chamber and a second cross-sectional area and a second depth of the apertures of the second set correspond to the second frequency.

14. The method of claim 13, further including:

concurrently reducing the first frequency and the second frequency.

15. The method of claim 12, wherein an aperture size of the first set of apertures is adjustable, and further including:

automatically adjusting the size of the apertures based on a speed of air flow across resonator, changing a resonant frequency of the resonator from the first frequency and second frequency of the audible noise.

16. The method of claim 12, wherein an aperture size of the first set of apertures is adjustable, and further including:

controlling the size of the apertures based on a voltage applied to a cooling system of the imaging system, which changes the frequency of the audible noise that is canceled.

17. The method of claim 12, wherein an aperture size of the first set of apertures is adjustable, and further including:

controlling the size of the apertures based on a speed of an intake blower or a fan the imaging system.

18. A non-transitory computer readable medium encoded with computer executable instructions, which when executed by a processor, causes the processor to: set a first speed of an intake blower or fan of an imaging system, wherein the intake blower or the fan produces audible noise; and set a size of an adjustable size aperture of resonator of an imaging system to resonate at a first frequency of the audible noise corresponding to the first speed.

19. The computer readable medium of claim 18, wherein the instructions further cause the processor to:

change the first speed to a second speed; and adjust the size of the adjustable size aperture of resonator of the imaging system to resonate at a second frequency of the audible noise corresponding to the second speed.

20. The computer readable medium of claim 18, wherein the instructions further cause the processor to:

adjust the size of the adjustable size aperture based on a voltage applied to the blower or the fan.

* * * * *